United States Patent [19]
Zanger et al.

[11] Patent Number: 5,470,312
[45] Date of Patent: Nov. 28, 1995

[54] IRRIGATION/ASPIRATION APPARATUS FOR SURGICAL PROCEDURES

[75] Inventors: Frank Zanger, Hayward; Edward R. Zaleski, Santa Ana; Mark Cole, Trabuco Canyon, all of Calif.

[73] Assignee: Allergan, Inc., Irvine, Calif.

[21] Appl. No.: 201,567

[22] Filed: Feb. 25, 1994

Related U.S. Application Data

[63] Continuation-in-part of Ser. No. 893,119, Jun. 3, 1992, abandoned.

[51] Int. Cl.⁶ .................................................. A61M 1/00
[52] U.S. Cl. ........................... 604/34; 604/27; 604/36; 128/DIG. 13
[58] Field of Search ..................... 604/27, 34, 35, 604/36, 39, 43, 93, 118, 249, 250, 131, 246; 128/DIG. 13

[56] References Cited

U.S. PATENT DOCUMENTS

| | | | |
|---|---|---|---|
| 4,037,604 | 7/1977 | Newkirk | 128/350 |
| 4,262,824 | 4/1981 | Hrynewycz | 222/450 |
| 4,332,322 | 6/1982 | Jaeshke et al. | 206/364 |
| 4,425,116 | 1/1984 | Bilstad et al. | 604/34 |
| 4,457,757 | 7/1984 | Molteno | 604/294 |
| 4,479,761 | 10/1984 | Bilstad et al. | 417/395 |
| 4,521,210 | 6/1985 | Wong | 604/8 |
| 4,523,679 | 6/1985 | Paikoff et al. | 206/370 |
| 4,537,305 | 8/1985 | Takanashi | 206/438 |
| 4,545,783 | 10/1985 | Vaughan | 604/259 |
| 4,627,833 | 12/1986 | Cook | 604/34 |
| 4,634,418 | 1/1987 | Binder | 604/8 |
| 4,722,724 | 2/1988 | Schocket | 604/8 |
| 4,735,610 | 4/1988 | Akkas et al. | 604/119 |
| 4,736,850 | 4/1988 | Bowman et al. | 206/570 |
| 4,750,901 | 6/1988 | Molteno | 604/8 |
| 4,798,580 | 1/1989 | DeMeo et al. | 604/30 |
| 4,856,339 | 8/1989 | Williams | 73/714 |
| 4,936,825 | 6/1990 | Ungerleider | 604/8 |
| 4,963,131 | 10/1990 | Wortrich | 604/34 |
| 5,106,366 | 4/1992 | Steppe | 604/30 |

*Primary Examiner*—Paul B. Prebilic
*Attorney, Agent, or Firm*—Walter A. Hackler

[57] ABSTRACT

An irrigation/aspiration apparatus is provided for use with surgical instrumentation requiring irrigation and aspiration of fluids and a peristaltic pump. The apparatus includes a housing and a manifold for connecting a transfer tube with aspiration and irrigation lines from the surgical instrumentation and with waste and supply lines. An opening the housing enables access to the transfer tube in order to control fluid flow therein. A diaphragm mounted to the housing and in fluid communication with the aspiration tube enables both pressure measurement and pressure control in the tubing when the housing is inserted into a drawer in the console and in operative engagement with a peristaltic pump head disposed therein.

16 Claims, 5 Drawing Sheets

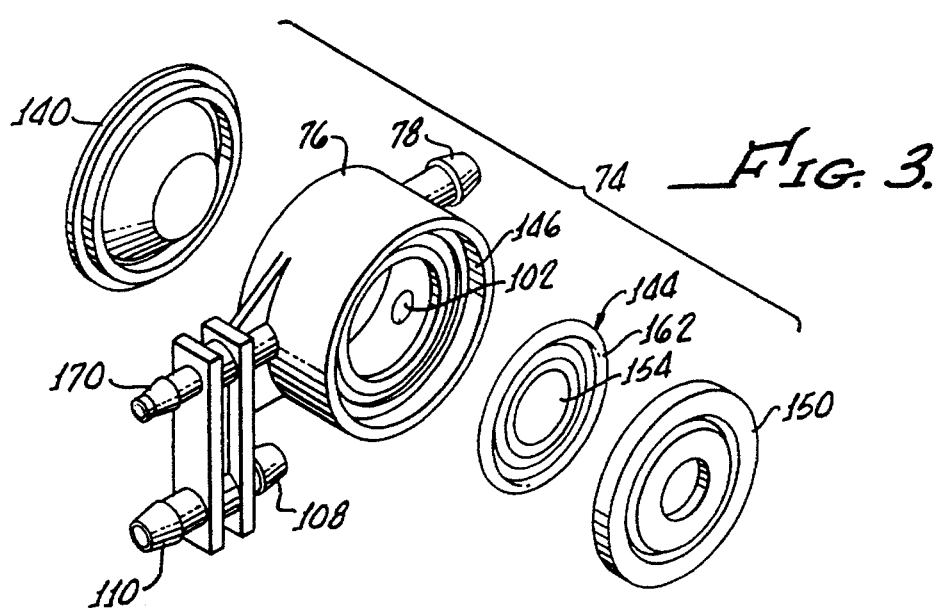
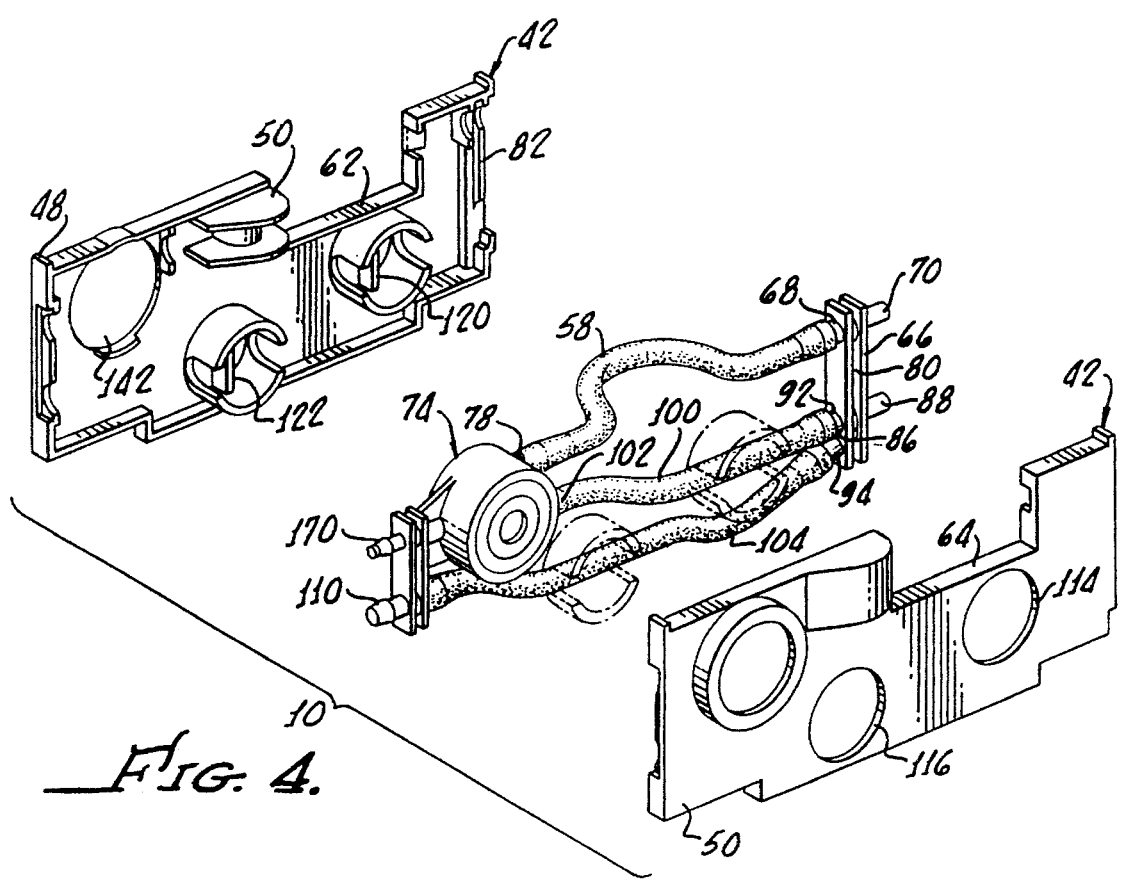

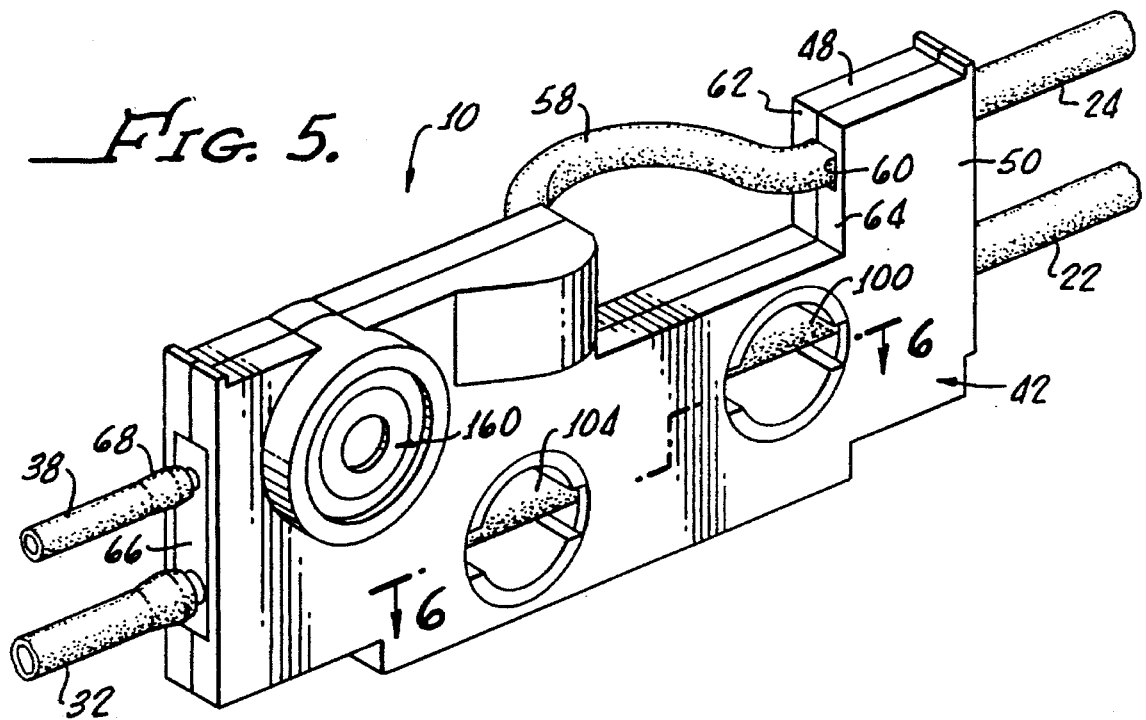

IRRIGATION/ASPIRATION APPARATUS FOR SURGICAL PROCEDURES

This application is a continuation-in-part of U.S. Patent application Ser. No. 07/893,119, filed Jun. 3, 1992, now abandoned.

The present invention generally relates to irrigation/aspiration apparatus for surgical procedures and more particularly relates to a tubing management system in combination with a surgical instrument for endophthalmic surgery for providing rapid pressure regulation and control.

The removal of cataracts, for example, involves surgery on a normally pressurized eye in which instruments are passed through a small incision at the edge of the cornea in order to access and remove opaque cataract material.

The cataracts may be fragmentized by cutting apparatus, vibratory apparatus, or the like, and the fragments are aspirated from the eye.

In order to maintain normal pressure within the eye, a balanced salt solution is supplied from an elevated chamber, the chamber being elevated to a position to provide proper head, or pressure.

The irrigation and aspiration of fluid through the eye must be carefully monitored in order to maintain normal pressure within the eye during surgical procedures. An under-pressure may cause distortion of the eye which often may interfere with surgical procedures. Over-pressure may cause damage to the eye and in extreme cases, rupture thereof.

As hereinabove noted, pressure in the eye may be controlled by the physical elevation of the chamber of balanced salt solution, which is connected to the surgical instrument. Aspiration fluid, on the other hand, is controlled in the eye with a peristaltic pump or other means of providing fluid flow.

Typical apparatus includes instrument console for controlling the flow of fluids. Various devices have been developed for the coordinated flow of fluids and some include a cartridge, tubing and management system, which may be disposable or autoclavable, for interconnecting from the various tubes and lines for proper irrigation and aspiration.

A general discussion of the advantages of this type of cassette is set forth in U.S. Pat. No. 4,713,051.

Cassettes, such as those described in U.S. Pat. No. 4,713,051, provide means for housing a portion of each of the irrigation and aspiration tubing, together with a drain bag structured so that all fluid and connections are precisely made to the equipment by insertion of the cassette into a console. Thus, the reliability of the fluid connections is enhanced.

While the prior art devices, such as the one described in U.S. Pat. No. 4,713,051, provide a significant step forward in art of tube management, these devices do not provide full cooperation with a surgical instrument utilizing irrigation and aspiration lines.

For example, during surgical procedures, often fragments of broken tissue can temporarily block an aspiration line. This may lead to a differential pressure which is typically accommodated by ceasing or slowing aspiration flow through regulation of the peristaltic pump connected to the aspiration line.

During aspiration of the nucleus, particles may restrict aspiration flow from the eye through the aspiration port, thereby occluding the tip. In an attempt to clear this occlusion, vacuum levels are increased to create a greater differential pressure across the occluding particle in an effort to move the particle downstream and away from the eye. Typically, particles require a much higher force to start movement than it takes to continue movement.

Once a particle moves, it creates a volume of fluid behind it to take up the space it once occupied. This volume may momentarily be larger than the volume of the eye (~3 cc), therefore producing a momentary dimpling of the eye. It has been shown that pressure sensing of this condition is well within the operation of the phaco machine. However, response to this condition is slow and therefore not effective by current methods not limited to stopping the aspiration pump and then reversing its rotation to compensate for differential after initial movement of the particle is achieved.

However, the tubing management system, in accordance with the present invention, facilitates the reversal of fluid flow in a surgical instrument's irrigation and aspiration lines. Naturally, this facilitates operating procedures and, at the same time, provides increased reliability of high pressure during an operation. In addition, by utilizing a quick-acting solenoid actuator positioned to actuate the cartridge diaphragm in a reverse action, it is possible to react to measured pressure rise and reduce the time for aspiration vacuum to reach ambient pressure. It is also possible for this same solenoid to be used as a short pulse reflux to clear occluded particles from the tip on demand by the surgeon.

SUMMARY OF THE INVENTION

Irrigation/aspiration apparatus in accordance with the present invention is suitable for use with surgical instrumentation requiring irrigation and aspiration of fluids.

Generally, the system includes a housing having means for both supporting an aspiration tube and enabling access thereto for contact with a peristaltic pump head and for connecting the aspiration tube with an aspiration line of a surgical device. Means are also provided for connecting an irrigation tube to both the aspiration line and an irrigation line of the surgical device.

Importantly, means are provided for enabling the regulation of irrigation fluid flow in the irrigation tube into both the irrigation and the aspiration lines. As hereinafter set forth, this structure enables back flushing of the surgical instrument through the aspiration line in order to remove blockages therefrom.

Structure of the present invention enables blockage removal without venting of the aspiration line as may be necessary in prior art devices. In this manner, pressure may be more precisely controlled during both normal aspiration of fluids from the surgical device aspiration tube and during back flushing of the irrigation fluid through the aspiration line.

The means for enabling the regulation of irrigation fluid flow includes transfer tubes interconnecting the irrigation tube with both the irrigation and aspiration lines and further means defining openings in housing for enabling access to the transfer tubes. More specifically, the means for enabling access to the transfer tubes includes bridge means spanning each opening, for enabling the transfer tubes to be compressed thereagainst in order to regulate the fluid flow therein.

Additionally, the apparatus according to the present invention includes means for enabling pressure measurement of the fluid in the aspiration tube. Pressure measurement is enabled by a diaphragm mounted to the housing in fluid communication with both the aspiration tube, the aspiration line and a transfer tube. The diaphragm includes means for removably coupling the diaphragm to an external transducer.

In this manners, the tubing management system, in accordance with the present invention, includes not only the tubing configuration hereinabove set forth, but also incorporated therewith the pressure measurement device, thus eliminating a separate tubing connection with an additional external device for measuring pressure.

Importantly, the apparatus includes means, including a diaphragm, for both measuring fluid pressure in the aspiration line and in response to the pressure measurement for abruptly changing the pressure of the fluid in the aspiration line by movement of the diaphragm.

Manifold means may be provided which are removably attached to the housing for connecting the transfer tubes with the aspiration and irrigation lines. This structure facilitates the organization and the assembly of the device.

BRIEF DESCRIPTION OF THE DRAWINGS

The advantages and features of the present invention will be better understood by the following description when considered in conjunction with the accompanying drawings in which:

FIG. 3 is an exploded perspective view of a diaphragm assembly for enabling fluid pressure measurement and regulation of pressure in an aspiration line;

FIG. 4 is an exploded perspective view of the cassette in accordance with the present invention;

FIG. 5 is a perspective view of the cassette fully assembled;

FIG. 6 is a cross-sectional view of the cassette showing compression of transfer tubes therein for controlling fluid flow;

DETAILED DESCRIPTION

Figure 1:
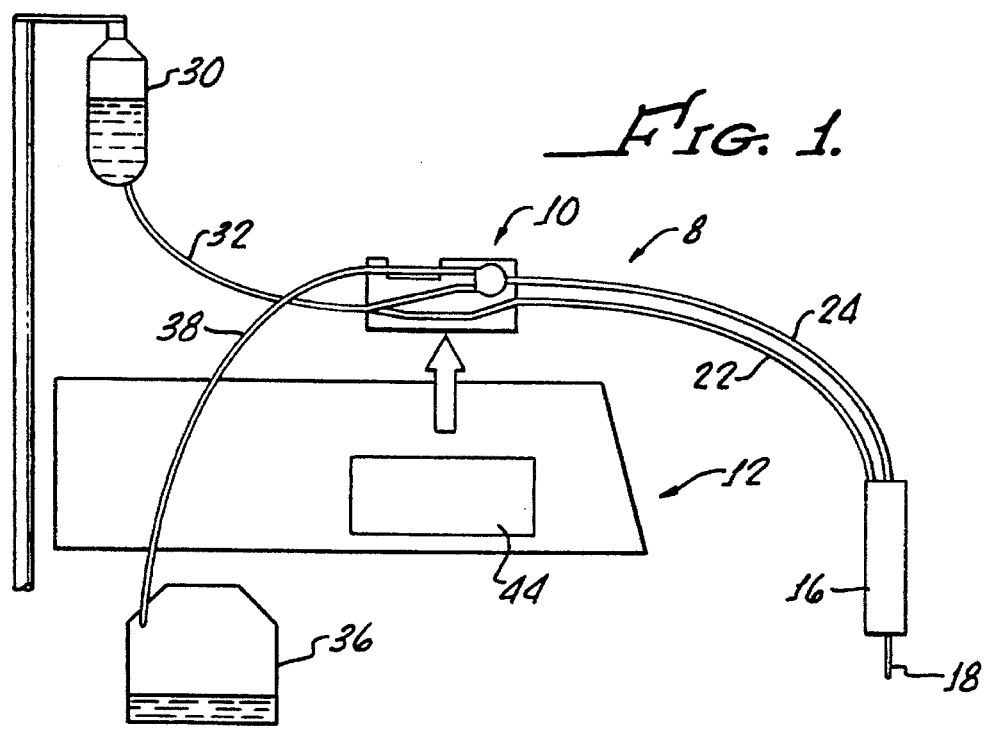
FIG. 1 is a schematic representation of the irrigation/aspiration apparatus, in accordance with the present invention, showing a tubing cassette as it may be interconnected with a surgical instrument, a saline solution supply, and a waste receptacle.

In FIG. 1, there is shown a cassette 10, in accordance with the present invention, suitable for use with instrument console 12, having a peristaltic pump head 14 (see FIG. 2) and a surgical instrument 16, with tip 18 (see FIG. 1).

Figure 2:
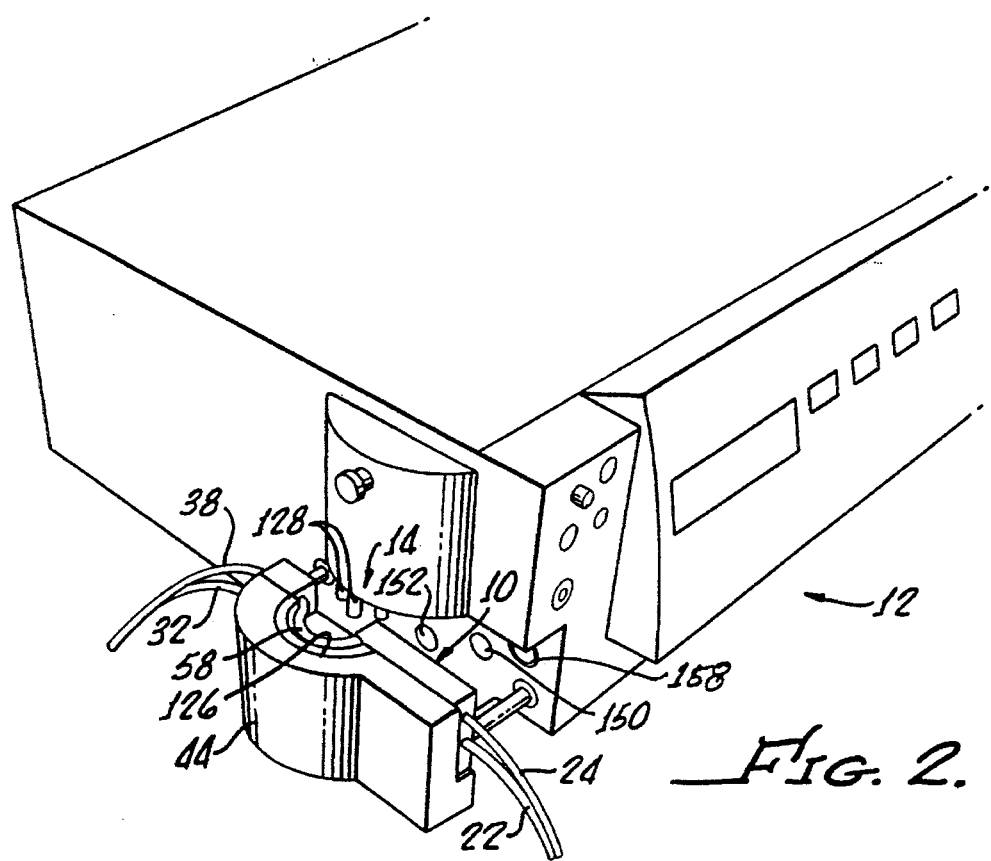
FIG. 2 is a perspective view of the cassette as it may be inserted into a console drawer.

As hereinabove described, the present invention is used in conjunction with the surgical instrument or handpiece 16 for ophthalmic surgery, requiring irrigation and aspiration of fluids. As will be hereinafter discussed in greater detail, the cassette 10 is connected with an irrigation line 22 and an aspiration line 24 for providing fluid communication between the surgical handpiece 16 and a source 30 of irrigation fluid through a line 32 and also with a waste receptacle 36 through a waste line 38. All these are diagrammatically represented in FIG. 1. As will be described hereinafter in greater detail, the cassette 10 includes a housing 42 (FIGS. 4 & 5) which is sized for insertion into a drawer 44 in the console 12 (FIG. 2).

The housing 42 may consist of the rear half 48 and a front half 50 which is formed from any suitable plastic material. If the cassette 10 is disposable, the rear and front halves 48 and 50 may be plastic welded or glued together to form the cassette 10. In this instance, a lower grade of plastic for the cassette 10 may be employed.

Alternatively, if the cassette is to be reused, the rear and front halves 48 and 50 may be snapped or screwed together in any suitable fashion in order to facilitate disassembly of the cassette 10. In this instance, the rear and front halves 48 and 50 should preferably be formed from a plastic, or other material, suitable for autoclaving.

The rear half 48 includes a channel 50 in order to provide a means for supporting an aspiration tube 58 when the rear half 48 is assembled to the front half to form the housing 42. Openings 62, 64 in the rear half and front half 48 and 50, enable access to the aspiration tube 58 for contact with the peristaltic pump head 14. A manifold 66 includes nipples 68, 70 which provide means for connecting the aspiration tube 58 with the waste line 38.

The diaphragm assembly 74 includes a housing 76 with an upper inlet 78 which provides a means for connecting the aspiration tube 58 to the aspiration line 24. The diaphragm assembly 74 will be described in greater particularity hereinafter.

The manifold 66 may be formed from a suitable plastic and include a slot 80 for enabling attachment of the manifold 66 to a rib 82 molded into the rear half 48 of the housing 42. A Y formed into the manifold 66 includes an external nipple 88 communicating with nipples 92, 94 which provides means for connecting the irrigation line 32 to both the aspiration line 24 and the irrigation line 22 of the surgical device 16.

An upper transfer tube 100 interconnects the nipple 92 with a lower inlet 102 in the diaphragm housing while a lower transfer tube 104 connected with the lower nipple 94 is connected by nipples 108, 110 to the irrigation line 22 of the surgical instrument 116.

The upper transfer tube 100 is centered in the opening 114 in the front half 50 and the lower transfer tube 104 is centered in opening 116 in the front half and the openings 114, 116 provide a means for enabling the regulation of irrigation fluid flow in the irrigation line 32 into both the irrigation line 22 and aspiration line 24 of the surgical instrument 16.

Bridges 120, 122 formed in the front half 50 and spanning the openings 114, 116 respectively provide a means for enabling the transfer tubes 100, 104 to be compressed thereagainst, as hereinafter described, in order to regulate the fluid flow in the transfer tubes 100, 104 and thereby divert irrigation fluid from the BSS line 32 into either the irrigation line 22 or aspiration line 24 of the surgical instrument 16.

As hereinabove described, the diversion of irrigation fluid from the line 32 into the aspiration line 24 of the surgical instrument is made in order to free blockages which may occur in the aspiration line 24 from time to time. Importantly, the irrigation of fluid is diverted through the diaphragm housing in order that the pressure thereof during back flushing of the aspiration line 24 may be monitored.

As hereinbefore noted, and as will be hereinafter discussed in greater detail, during aspiration the tip 18 may become occluded and this causes an abrupt change in the pressure of the fluid in the aspiration tube 58.

Turning now to FIG. 2, the console drawer 44 is sized for accepting the cassette 10 in the manner illustrated with the aspiration tube 58 to a curved portion 126 of the drawer 44 and forced against pump head rollers 14 when the drawer 44 is closed with the cassette 10 therein.

Any conventional peristaltic pump head 14 with rollers 14 may be utilized in conjunction with the curved surface 126 to effect a peristaltic-type pumping of fluid from the aspiration line 24 of the surgical handpiece 16 when the pump head is rotated. The pump head and curved surface may be as described in U.S. Pat. No. 5,230,614. This patent is to be incorporated into the present application in toto by this specific reference thereto.

Also included in the console are solenoid-activated plungers 130, 132 which, when activated, move outwardly from the console to engagement with the transfer tubes 100, 104 respectively through the holes 114, 116, in order to compress the transfer tubes 100, 104 against the bridges 120, 122, respectively, in order to divert irrigation fluid from the irrigation line 32 to the diaphragm housing 74 or directly into the irrigation line 22 of the surgical handpiece 16.

The plungers 130, 132 may be activated and operated in any conventional manner through switches in the console 12 or by remote control, as may be desired.

Returning to FIG. 3 & 4, the diaphragm housing 74 generally includes a cap 140, which may be ultrasonically welded to the rear half 48 in an opening 142 therein. The diaphragm 144 is disposed over an opening 146 in the front of the housing 76 and secured and sealed therein by the retainer 150 which is ultrasonically sealed to the housing 76. A ferromagnetic disk. 154 is bonded to the diaphragm 144 and provides means for removably coupling the diaphragm to a magnet 158, see FIG. 2, disposed in the instrument console 12 when the cassette 10 is inserted into the instrument console drawer 44.

As more completely described hereinafter the transducer magnet 158 is coupled to force transducer 160, providing a means for measuring force exerted by fluid within the diaphragm housing on one side 162 of the diaphragm 144, independent of the diaphragm position. This cited reference, "Pressure Transducer Interface," is to be incorporated into the present application by this specific reference thereto.

As pointed out in this reference, this force measurement eliminates a number of practical problems associated with the changing characteristics of the diaphragm as a function of its position. A permanent magnet attached to the transducer couples with the ferromagnetic disk 154 when the cassette 10 is disposed in the drawer 44 and closed so that the magnet 166 is abutted with the disk 154 to effect the coupling therebetween. Simultaneously, upon closing the drawer, plungers 130, 132 are positioned in a spaced apart relationship with the transfer tubes 100, 104 in order that engagement therewith may be effected by the movement, or displacement, of the plungers so as to selectively engage and compress the transfer tubes 100, 104 against the bridges 120, 122 respectively.

The diaphragm housing 76 may be coupled to the irrigation line 22 by means of the nipple 170 and therefore enables irrigation fluid diverted through the transfer tube 100 by sealing of the transfer tube 104 against the bridge 122, into the aspiration line 24. Alternatively, when the transfer tube 100 is compressed against the bridge 120, irrigation fluid flows into the irrigation line 24 through the transfer tube 104.

When irrigation fluid is diverted into the aspiration line 24, the peristaltic pump head may be stopped to prevent aspiration of the irrigation fluid directly from the diaphragm housing 76.

It is important that during both normal flow of irrigation fluid through the transfer tube 104 and during the back flush of fluids through the transfer tube 100 into the aspiration line 24, that the diaphragm assembly 74 is operative for enabling pressure measurement on a continuous basis in order to monitor the pressure.

Figure 7:
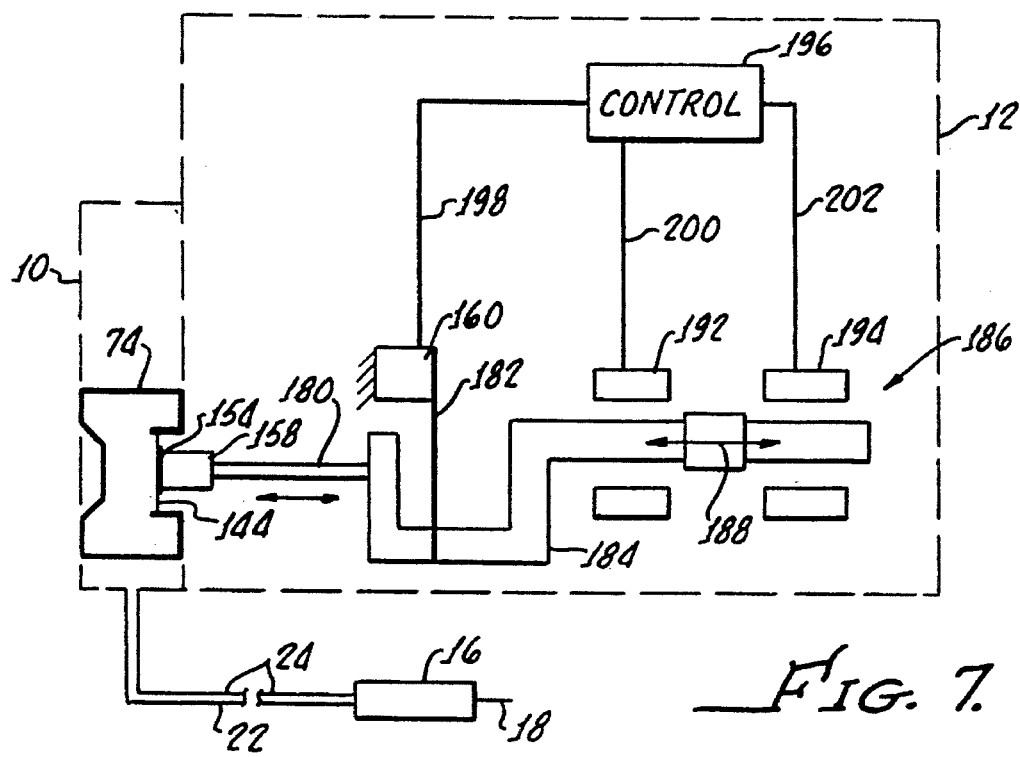
FIG. 7 is a block diagram illustrating the cassette in engagement with an instrument console showing a pressure transducer and a solenoid for enabling a quick response to changes in fluid pressure.

Turning now to FIG. 7, there is shown a block diagram illustrating the cassette 10 in engagement with the instrument console 12 showing the diaphragm 144 removably coupled to the force transducer 160 through the ferromagnetic disc 154, transducer magnet 158 and lever arm 180. A transducer arm 182 may be attached in an abutting relationship with the lever arm 180 and a solenoid piston 184, in order to provide a means for both measuring the fluid pressure in the aspiration line 24 and in response to the pressure measurement for abruptly changing the pressure of fluid in the aspiration line by movement of the diaphragm 144.

Abrupt movement of the diaphragm 144 is accomplished through the use of a solenoid 186 which, as shown in FIG. 7, rapidly moves the solenoid arm 184 in a lateral direction, indicated by the double-headed arrow 188 through energizing coils 192, 194 on the solenoid 186.

A conventionally designed control system 196 receives output from the transducer 160 through a line 198 and accordingly controls coils 192, 194 through lines 200, 202.

Figure 8:
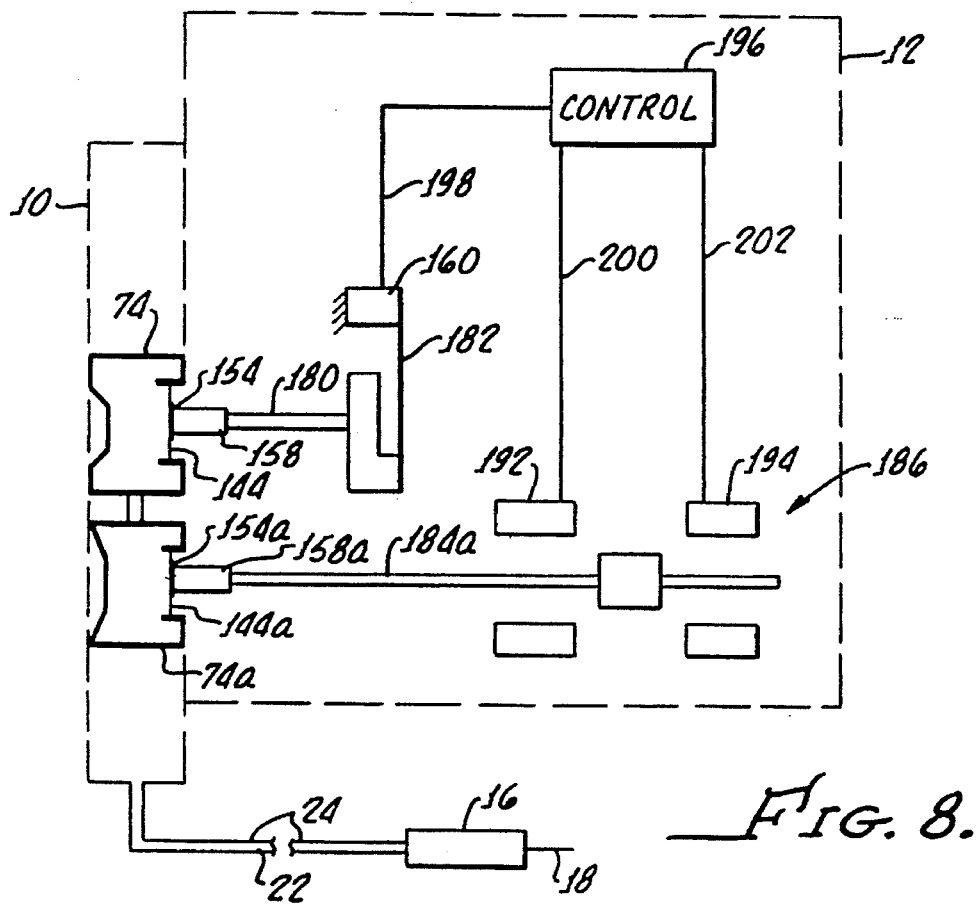
FIG. 8 is a block diagram illustrating an alternative embodiment of the present invention shoeing two diaphragms.

An alternative embodiment of the present invention is shown in FIG. 8, in which a second diaphragm 144a disposed in housing 74a is utilized to separately abruptly change the pressure in the aspiration line 24. In this embodiment, a solenoid arm 184a is coupled to the diaphragm 144a through a magnet 158a and a ferromagnetic disc 154a. Thus, in operation, the diaphragm 144 is utilized through the transducer 160 to measure the pressure, and the diaphragm 144a is utilized to abruptly change the pressure by way of actuating the coils 192, 194 of the solenoid 186, with the operation being controlled by the control system 196. It should be appreciated that in FIGS. 7 and 8, like referenced numerals or characters refer to identical or corresponding parts throughout the several views.

Figure 9:
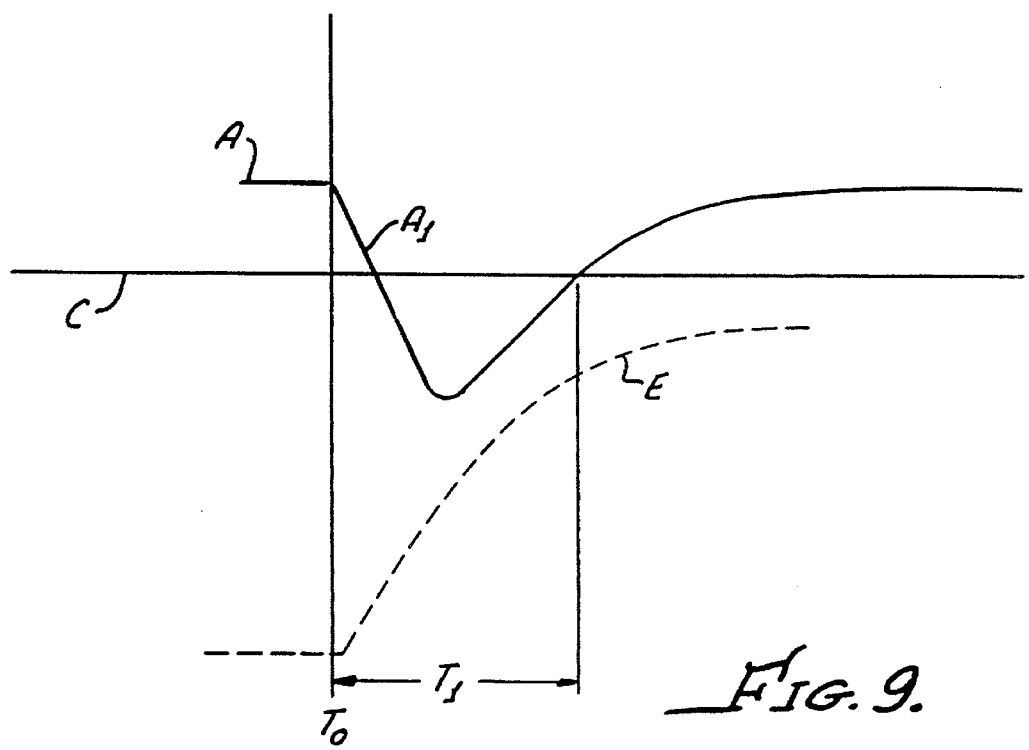
FIG. 9 is a plot of pressure vs. time without the solenoid apparatus shown in as FIG. 7.
Figure 10:
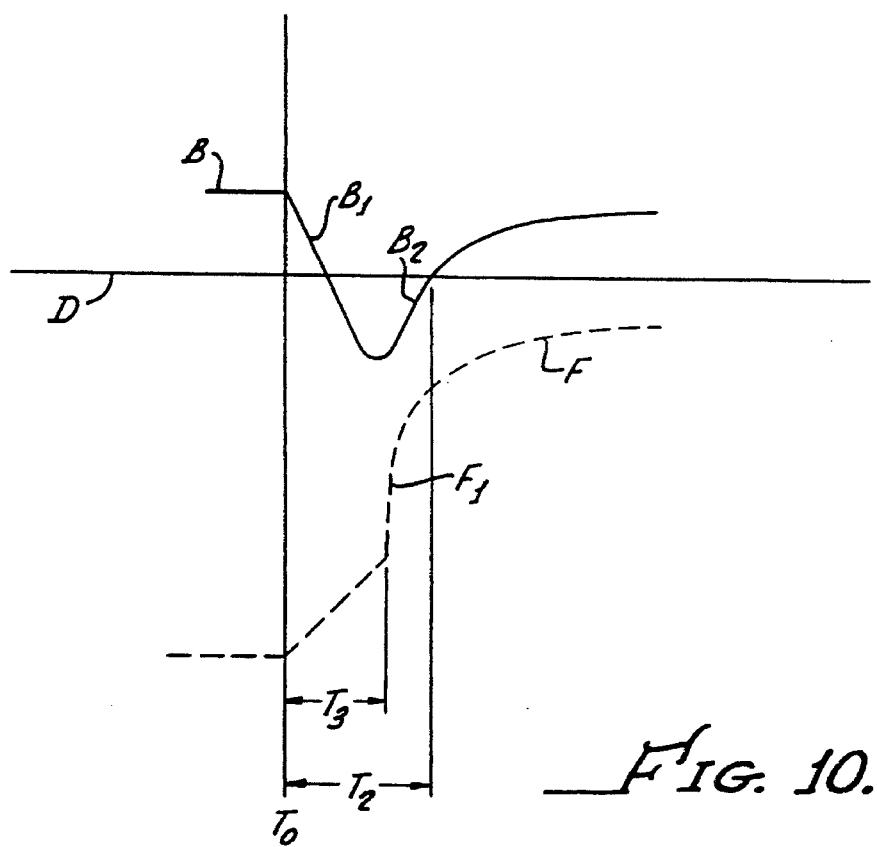
FIG. 10 is a plot of pressure vs. time with the solenoid apparatus as shown in FIG. 7.

Turning now to FIGS. 9 and 10, there is shown respectively plots of pressure vs. time, without the solenoid apparatus 186 and with the solenoid apparatus 186 operating to provide abrupt compensation for pressure changes in the aspiration line. FIGS. 9 and 10 are plots A, B of intraocular pressure (IOP) as a function of time with an ambient pressure, shown by the lines C and D in FIGS. 9 and 10 respectively. When an occlusion occurs at $T_o$, the intraocular pressure drops sharply below the ambient pressure C, D as shown by the line segments $A_1$, $B_1$.

Pressure in the aspiration line, as indicated by the dashed lines E, F in FIGS. 9 and 10, respectively, increases rapidly.

However, when the diaphragm 144 is not actuated by the solenoid 186, the intraocular pressure does not recover to ambient pressure C for a lapse of time $T_1 \cdot T_1$ may be in the order of about 1.5 to about 3.0 seconds, or greater, for a given vacuum of about 315 mm mercury @ $T_o$.

This is to be compared with the aspiration pressure as indicated by dashed line F in FIG. 10, in which the control system 196 operates the solenoid 186 in response to the drop in the intraocular pressure detected by the diaphragm 144 and pressure transducer 160 to provide a quick, or abrupt, movement of the diaphragm 144 by the solenoid to increase the aspiration line pressure, as indicated by the line segment $F_1$ which causes a rapid recovery of the intraocular pressure, as indicated by the line segment $B_2$, so that the intraocular pressure B recovers to ambient pressure D in a time $T_2$ which may be approximately 0.5 seconds, or less. Also shown in FIG. 10 is a time $T_3$ which bay be about 0.02 seconds, or less, which indicates the actuation of the solenoid 86 for changing the pressure in the aspiration line and changing the intraocular pressure.

Thus, the irrigation/aspiration apparatus in accordance with the present invention is able to respond quickly in order to maintain intraocular pressure.

It should also be appreciated that while FIGS. 9 and 10 illustrate a displacement of the diaphragm 44 rapidly increasing the pressure, the solenoid 186 may also be used as a short pulse reflux to clear fluid particles from tip 18 on demand by a surgeon.

Although there has been hereinabove described an irrigation/aspiration apparatus, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. An irrigation/aspiration apparatus for use with surgical instrumentation requiring irrigation and aspiration of fluids and a peristaltic pump, the apparatus comprising:

an aspiration tube;

a housing comprising means for both supporting the aspiration tube and enabling access thereto for contact with a peristaltic pump head and for connecting said aspiration tube with an aspiration line of a surgical device;

means for connecting a supply line to both the aspiration line and an irrigation line of the surgical device;

means for enabling the regulation of irrigation fluid flow in said supply line into both said irrigation and aspiration lines of the surgical device; and means, comprising a diaphragm, for both measuring fluid pressure in the aspiration line and for abruptly changing the pressure of the fluid in the aspiration line by movement of the diaphragm in response to the pressure measurement.

2. The apparatus according to claim 1 wherein said means for enabling the regulation of irrigation fluid flow comprises transfer tubes interconnecting said irrigation line with both said irrigation and aspiration lines and means, defining openings in said housing, for enabling access to the transfer tubes.

3. The apparatus according to claim 2 wherein said means for enabling access to the transfer tubes further comprises bridge means, spanning each opening, for enabling the transfer tube to be compressed thereagainst in order to regulate fluid flow therein.

4. The apparatus according to claim 1 wherein said diaphragm is mounted to said housing and in fluid communication with said aspiration line through the aspiration tube, and said apparatus further comprises a pressure transducer, a solenoid, and means for removably coupling said diaphragm to the pressure transducer and the solenoid.

5. The apparatus according to claim 4, further comprising control means, responsive to said pressure transducer for actuating said solenoid in order to move said diaphragm to regulate fluid pressure in said aspiration line.

6. An irrigation/aspiration apparatus for use with surgical instrumentation requiring irrigation and aspiration of fluids and a peristaltic pump, the apparatus comprising:

a housing;

manifold means, removably attached to said housing, for connecting a transfer tube with aspiration and irrigation lines from the surgical instrumentation and with waste and supply lines;

means, defining an opening in said housing, for enabling access to a transfer tube connected to the aspiration line for engagement with a peristaltic pump head;

means for enabling control of fluid from said supply line to both said aspiration and irrigation lines through said transfer tubes; and first diaphragm means for measuring fluid pressure in the aspiration line through the transfer tube, and second diaphragm means responsive to the pressure measurement for abruptly changing the pressure of the fluid in the aspiration line by movement of the diaphragm.

7. Irrigation/aspiration apparatus according to claim 6 wherein said means for enabling the control of fluid flow comprises means, defining openings in said housing, for enabling access to the transfer tubes.

8. Irrigation/aspiration apparatus according to claim 7 wherein said means for enabling access to the transfer tubes further comprises bridge means, spanning each opening, for enabling the transfer tubes to be compressed thereagainst in order to regulate fluid flow therein.

9. The apparatus according to claim 6 further comprising pressure transducer means, in an operative relationship with said first diaphragm means, for generating a pressure signal corresponding to fluid pressure in said aspiration tube, solenoid means, in an operative relationship with said second diaphragm means, for moving the second diaphragm in order to change pressure in the aspiration tube, and control means, responsive to said pressure transducer, for actuating the solenoid means.

10. Irrigation/aspiration apparatus according to claim 6 wherein said first diaphragm means comprises a first diaphragm mounted to said housing and in fluid communication with said aspiration tube, said first diaphragm means including means for removably coupling said first diaphragm to an external transducer, and said second diaphragm means comprises a second diaphragm mounted to said housing and in fluid communication with said aspiration tube, said second diaphragm means including means for coupling said second diaphragm to an external solenoid.

11. Irrigation/aspiration apparatus for use with surgical instruments requiring irrigation and aspiration of fluids and an instrument console having a peristaltic pump head and an opening for access thereto, the apparatus comprising:

a housing adapted for insertion into the instrument console opening and comprising means for both supporting an aspiration tube and for enabling operational contact therewith by said peristaltic pump head when the housing is inserted into the instrument console opening;

a diaphragm attached to said housing and in fluid communication with said aspiration tube;

a pressure transducer disposed in said instrument console;

a solenoid disposed in said instrument console; and means, attached to said diaphragm, for removably coupling said diaphragm to both the pressure transducer and the solenoid, when said housing is inserted into the instrument console opening.

12. Irrigation/aspiration apparatus according to claim 11 wherein said means for enabling the regulation of irrigation fluid flow in said irrigation tube into both said irrigation and aspiration lines.

13. Irrigation/aspiration apparatus according to claim 12 wherein said means for enabling the regulation of irrigation fluid flow comprises transfer tubes interconnecting said irrigation line with both said irrigation and aspiration lines and means, defining openings in said housing, for enabling access to the transfer tubes.

14. Irrigation/aspiration apparatus according to claim 13 wherein said means for enabling access to the transfer tubes further comprises bridge means, spanning each opening, for enabling the transfer tube to be compressed thereagainst in order to regulate fluid flow therein.

15. Irrigation/aspiration apparatus according to claim 11 wherein said means for removably coupling said diaphragm comprises a ferromagnetic plate attached to said diaphragm and a magnet coupled to said pressure transducer and said solenoid.

16. Irrigation/aspiration apparatus according to claim 15 wherein said magnet comprises a permanent magnet.

* * * * *